(12) United States Patent
Alexander (10) Patent No.: US 7,833,780 B2
(45) Date of Patent: Nov. 16, 2010

(54) VIRAL DIAGNOSTIC METHOD AND WELL FOR USE IN SAME

(76) Inventor: Robert Alexander, 9 Alder Court, Park Orchards, Victoria 3114 (AU)

(*) Notice: Subject to any disclaimer, the term of this patent is extended or adjusted under 35 U.S.C. 154(b) by 0 days.

(21) Appl. No.: 11/908,101

(22) PCT Filed: Mar. 10, 2006

(86) PCT No.: PCT/AU2006/000325

§ 371 (c)(1),
(2), (4) Date: Sep. 13, 2007

(87) PCT Pub. No.: WO2006/094364

PCT Pub. Date: Sep. 14, 2006

(65) Prior Publication Data

US 2008/0166702 A1 Jul. 10, 2008

(30) Foreign Application Priority Data

Mar. 10, 2005 (AU) .............................. 2005901141

(51) Int. Cl.
*C12Q 1/70* (2006.01)
*C12Q 1/02* (2006.01)
*C12P 39/00* (2006.01)
*C12M 1/36* (2006.01)
*C12N 5/00* (2006.01)
*A01N 63/00* (2006.01)
*A61K 39/12* (2006.01)
*A61K 36/00* (2006.01)

(52) U.S. Cl. .................. 435/288.1; 435/29; 435/42; 435/395; 435/5; 424/204.1; 424/93.6

(58) Field of Classification Search .................. None
See application file for complete search history.

(56) References Cited

U.S. PATENT DOCUMENTS 5,180,555 A 1/1993 Monget

FOREIGN PATENT DOCUMENTS

| AU | 2001100242 A4 | 8/2001 |
| JP | 62051977 A | 3/1987 |
| WO | 9005903 A | 5/1990 |

OTHER PUBLICATIONS

Corning Corp. Cell Culture Selection Guide—Life Sciences, 2002, p. 7 extracted.*

* cited by examiner

*Primary Examiner*—Zachariah Lucas
*Assistant Examiner*—Benjamin P Blumel
(74) *Attorney, Agent, or Firm*—Brooks Kushman P.C.

(57) ABSTRACT

The present invention relates to a single flat-based well suitable for use in a viral diagnostic method. More particularly, the well has a planar or flat base, as opposed to a curved base. The invention also relates to a viral diagnostic method that employs such single wells. In an embodiment of this method a specially developed tissue culture medium supplemented with hormones and enzymes is employed.

16 Claims, 4 Drawing Sheets

| VIRUS DETECTED | Row/Column | CELLLINES | Remove on day |
|---|---|---|---|
| PI1 | 1 | LLC-MK2 | 2 |
| PI2 | 2 | LLC-MK2 | |
| PI3 | 3 | LLC-MK2 | |
| INF A | 4 | MDCK | 2 |
| INF B | 5 | MDCK | |
| RSV | 6 | Hep2 | 2 |
| AD, VZ | 7 | A549 | 2.4 |
| RUBELLA | 8 | RK13 | 4 |
| CMV | 9 | MRC-5 | 2 |
| HSV1, 2 | 10 | MRC-5 | 1-2 |
| POLIO, ENTERO | 11 | MRC-5 | 5-7 |
| ECHO, COXACKIE | 12 | MRC-5 | |

FIGURE 4

VIRAL DIAGNOSTIC METHOD AND WELL FOR USE IN SAME

FIELD OF THE INVENTION

The present invention relates to a single flat-based well suitable for use in a viral diagnostic method. More particularly, the well has a planar or flat base, as opposed to a curved base. The invention also relates to a viral diagnostic method that employs such single wells. In an embodiment of this method a specially developed tissue culture medium supplemented with hormones and enzymes is employed.

BACKGROUND OF THE INVENTION

Conventional diagnostic procedures for identifying viruses include seeding containers with particular cell lines selected on their sensitivity to certain viruses and then inoculating the cell culture with a biological sample putatively containing a virus. Such biological samples include among other things saliva, urine, feces, cerebrospinal fluid (CSF), respiratory fluids and swabs such as those from the mouth, nasal cavity, throat, skin and genitals. The inoculated cell culture is then incubated and the cells examined for cytopathic effects induced by the virus. As certain viruses only grow on certain cells, the virus can be identified on the basis of the cell type in which it either induces a cytopathic effect (CPE) or does not induce a cytopathic effect.

There are a number of alternative protocols to this procedure including subjecting cells which have been inoculated with a virus preparation by trypsonisation to remove the cells, followed by virus detection using monoclonal antibodies specific for viral-derived polypeptides which are labeled with a reporter molecule such as a fluorescein (FITC) molecule. A further alternative is to include a cover slip within a culture tube in order to enhance recovery of the cells.

The conventional (or traditional—drum) method utilizes screw cap tubes which are seeded with appropriate cell lines. After the cells reach about 80% confluency the tube is inoculated with an appropriate specimen and monitored for CPE for up to three weeks. Daily monitoring of CPE is required for the first week. Less frequent monitoring is necessary for the second and third weeks. Often, blind passage is required to enhance virus recovery.

One of the disadvantages of this method is that it is time and labour intensive because daily monitoring of the tubes is required. Generally, two people inspect the same tube for CPE by light microscope to avoid subjectivity. In addition, not all viruses cause a visible CPE and those which do not are unable to be detected by this method. Furthermore, CPE formation monitored in the conventional tube method is highly dependent on the sensitivity of the cell lines and the capability of the virus to produce visible CPE. Toxicity of the specimen may also disadvantageously produce changes similar to viral CPE giving a false result. Also, some viruses produce CPE only after a long period of time (for example, Cytomagalovirus (CMV)). Thus, as results obtained by the conventional tube method are predominantly based on CPE detection and are not routinely confirmed by any other method, inaccurate diagnosis can occur. Another limitation of the conventional tube method is that it is difficult to use more than 2 or 3 tubes per specimen due to the resulting accumulation of tubes. For example, 40 specimens per day would create 500 tubes to analyze in the first week alone.

The shell vial method is currently the most advanced method utilized by those in the art for virus recovery. This method employs the use of a 5 ml plastic vial (shell vial), 16 mm in diameter which has a translucent lid. Following an appropriate treatment, a round (13 mm) cover slip is inserted into the vial. The vial is then seeded with a sensitive cell line which grows a monolayer on the cover slip. When the cell monolayer reaches about 80-90% confluency, the medium is discarded, the monolayer inoculated with the patient's specimen and the vial incubated. Then, the incubated vial is monitored for CPE, followed by the removal of the cover slip. The slip can then be fixed to a microscope slide and stained with monoclonal antibodies.

The advantage of the shell vial method is that virus recovery can be enhanced by centrifugation of vials after inoculation which can shorten the length of time taken to obtain results to as little as 2-3 days. Further, using the shell vial method there is no need to wait for visible CPE. The cover slip can be removed on the second or third day and stained with appropriate monoclonal antibodies and results confirmed using antibody-antigen staining.

However, the shell vial method also has a number of disadvantages. It is time consuming as the cover slips require special treatment; such as multiple washings with detergent and acetone followed by washing in distilled water and sterilization. The cover slips also have to be manually inserted into the vials. Further, if immunofluorescent staining is necessary, the procedure becomes even more complicated and time consuming. The medium from the shell vial has to be discarded and the cover slip manually removed using specific forceps, air-dried and fixed to a microscope slide, using vacuum grease. The removal of cover slips is tedious, since the cover slips may be broken by rough manipulation or unintentionally turned and fixed to the microscope slide with the monolayer upside down. Another complication may arise if the seeded cells also grow on the bottom of the cover slip, thus causing the cover slip to fix to the vial and making removal of the cover slip very difficult. Practically, as for the conventional tube method, using the shell vial method it is impossible to use more than 2 or 3 tubes per specimen due to the accumulation of tubes (i.e. 40 specimens per day creates 500 shell vials per week). Further, a large amount of monoclonal antibodies is required for immunofluorescence staining in order to cover the round 13 mm cover slip.

The 96 well plate method is another method which is used only in limited cases for recovery of viruses which grow on the same cell line. For example, if the wells are seeded with LLC-MK2 cell line the recovery of parainfluenza and also influenza viruses is possible. The 96 well plate method has advantages in that it is relatively easy to inoculate seeded cell lines with a particular specimen. Further, a large number of specimens can be inoculated onto the same plate and enhancement by centrifugation is also possible. Still further, the 96 well plate method only utilizes a small amount of media (0.3 ml instead of 1-1.5 ml used in the shell vial method), antigen-antibody techniques may be used for confirmation of results and the method also enables easy to "read" monitoring of CPE.

However, the 96 well plate method also has its disadvantages. The whole plate must be used for antigen-antibody detection which is not generally practical and the entire plate has to be used on the same day, even when the number of specimens is smaller than required for the whole plate. This means that for each day a new set of different plates must be used. This disadvantageously results in a situation where, once the detection is completed, there are no remaining cells available for a repeat procedure in case of an error or after a prolonged incubation period. Further, commonly only one or two different cell lines can be used per plate and the same type of specimen inoculated onto the plate.

Single well methodology, as described in Australian Innovation Patent No. 2001100242, alleviates problems associated with the conventional methods described above and provides an alternative, effective and economical process for conducting viral diagnosis. The disclosure of that patent is incorporated herein in its entirety by reference.

Flat-based wells are known to provide certain advantages when used in the context of diagnostic assays. In particular, they provide for more precise analysis compared with, say, round or curved-based wells. However, simple flat-based wells also have a disadvantage in that a meniscus tends to form in the base of the well resulting in uneven distribution of solution across the base of the well. In light of this, the inventor has developed a flat-based well that alleviates this problem as described below.

SUMMARY OF THE INVENTION

Accordingly, in a first aspect the invention provides a flat-based well for use in an assay, the well comprising:
- a main chamber having an opening to receive a liquid sample, side walls extending from the opening and a chamber base; and
- a sub-chamber extending from the chamber base of the main chamber and being adapted to receive a predetermined amount of the liquid sample, wherein the sub-chamber has a flat base.

Advantageously, this arrangement ensures that a liquid sample placed in the sub-chamber may not form a meniscus up the side-walls of the main chamber. Rather, a liquid sample placed in the sub-chamber may retain a convex surface extending from the sub-chamber towards and/or into the main chamber. The arrangement also ensures that the base surface on which any liquid sample rests is flat, providing for more precise analysis as previously described above.

In another embodiment the invention provides a well unit, comprising one or more of single flat-based wells in accordance with the invention.

In a further embodiment the invention provides a method of performing an assay, said method comprising using a single flat-based well in accordance with the invention or using a well unit in accordance with the invention.

Yet another aspect of the invention provides a method of detecting a virus, said method comprising:
- providing one or more single flat-based wells in accordance with the invention as described herein seeded with a preselected cell line;
- inoculating a specimen to be analyzed in the one or more wells; and
- examining for one or more preselected viruses in the one or more wells.

In a further embodiment the invention provides a method for detecting a virus said method comprising:
- providing a single flat based well in accordance with the invention as described herein seeded with a cell line suitable for virus inoculation;
- specific pre-treatment of a specimen to obtain a sample that potentially contains a virus to be detected;
- inoculating the cell line with the sample;
- incubating the inoculated cell line;
- replacing sample media of the inoculated cell line with a virus recovery media comprising a cell culture medium supplemented with at least one hormone and at least one enzyme;
- incubating the inoculated cell line; and
- analyzing the incubated cell line for the presence of a virus.

In yet another embodiment the invention provides for use of a single flat-based well or use of a well unit in accordance with the invention, in an assay.

Another aspect of the invention provides for use of a single flat-based well in accordance with the invention in a method of detecting a virus, said method comprising:
- providing one or more single flat-based wells in accordance with the invention as described herein seeded with a preselected cell line;
- inoculating a specimen to be analyzed in the one or more wells; and
- examining for one or more preselected viruses in the one or more wells.

In a further embodiment the invention provides for use of a single flat-based well in accordance with the invention in a method for detecting a virus, said method comprising:
- providing a single flat based well in accordance with the invention as described herein seeded with a cell line suitable for virus inoculation;
- specific pre-treatment of a specimen to obtain a sample that potentially contains a virus to be detected;
- inoculating the cell line with the sample;
- incubating the inoculated cell line;
- replacing sample media with a virus recovery media comprising a cell culture medium supplemented with at least one hormone and at least one enzyme;
- incubating the inoculated cell line; and
- analyzing the incubated cell line for the presence of a virus.

BRIEF DESCRIPTION OF THE DRAWINGS

Embodiments of the present invention are illustrated in the accompanying non-limiting drawings in which.

DETAILED DESCRIPTION OF THE INVENTION

The main chamber and sub-chamber may take any suitable form, provided that the sub-chamber extends from the chamber base of the main chamber. The single flat-based wells may take any suitable form, provided that the base of the well that receives the specimen is flat. For example, the wells may have a circular, square, triangular or hexagonal cross section. Also, the wells may be uniform in cross section along their height. Alternatively, the wells may taper towards their top or their bottom end. It will be appreciated that the wells will be formed using standard materials as used for conventional micro titre tray assemblies and by standard techniques.

Preferably, the main chamber has a square cross section and the sub-chamber has a circular cross section. The arc of the circular side of the sub-chamber, in this embodiment, preferably extends to the edge of each side of the main chamber. This will be appreciated from the accompanying figures which better illustrate this feature.

Typically the sub-chamber can hold a predetermined volume of about 30 μl in total, such that in the sub-chamber a liquid sample forms a droplet advantageously having a convex surface extending from the sub-chamber opening and further, such that the depth of the liquid is substantially constant through the sub-chamber, thus alleviating the disadvantage of a liquid sample that is placed in a well and forms a meniscus up the side walls of the well.

Preferably the ratio of the height of the main chamber as compared to the sub-chamber is 10:1 and the ratio of the width of the main chamber as compared to the sub-chamber is between 2:1 and 1:1. In a preferred embodiment, the height of the well is 11 mm, including a 10 mm height for the main chamber and a 1 mm depth for the sub-chamber. The width of the well is generally 8 mm, and has a wall thickness of about 1 mm and the internal width of the sub-chamber is about 6 mm. Thus the main chamber typically allows for a volume of about 360 µl and the sub-chamber typically allows for a volume of about 28.3 µl.

This particular embodiment may equally provide advantages if the wells are used in a well unit. For example, where a number of the wells are joined and not used individually. Thus, according to an alternative embodiment of the invention there is provided a well unit including more than one of the wells in accordance with the invention. A well unit can be for example, a 96 or 48 well plate configuration or a unit as described in Australian Innovation Patent No. 2001100242.

It will be appreciated by one skilled in the art that in the context of some assay methods where the wells are required to be inserted into a plate that the wells could be provided with means for facilitating engagement with the well plate they are to be inserted into. For example, the wells may be tapered as mentioned above to provide a friction fit in a receptacle of the well plate. Alternatively, the wells may be provided with a rib or an indentation or groove that cooperates with the receptacle of the plate that the well is to be inserted into.

In some instances, wells may be dislodged from the well plate during analysis or during transportation of the plate. As such, in a preferred embodiment the wells include some form of identification, such as colour coding or marking. The wells may, for example have markings that indicate their position (column and row) on the plate.

To assist analysis, the wells may also include a flat-base that is provided with marked divisions. For example, the flat-base of each well may include a cross hair that divides the flat-base into four quarters. Thus, analysis of one quarter will provide data useful for the analysis of the flat-base as a whole. It will be appreciated that any number of divisions of the flat-base may be suitable for this purpose.

The wells of the invention have an extremely wide variety of uses. Broadly speaking, the wells of the present invention are useful in assays. The skilled artisan will recognize that such assays include, but are not limited to Enzyme-linked Immunosorbent Assays (ELISA), bacterial cell culture, PCR amplification techniques, protein crystallization techniques, anti-viral susceptibility testing and chemical and drug screening techniques. In one embodiment for example, the wells of the invention are useful for viral diagnostic assays.

As used herein, reference to an assay should be understood as reference to any conventional laboratory techniques which utilize micro titre wells.

Accordingly, in a second aspect the invention provides a method for detecting a virus said method comprising:
  providing one or more single flat-based wells in accordance with the invention as described herein seeded with a preselected cell line;
  inoculating a specimen to be analyzed in the one or more wells; and
  examining for one or more preselected viruses in the one or more wells.

In one embodiment the invention provides a method of performing an assay said method using one or more single flat-based wells in accordance with the invention as described herein. Preferably the assay is a viral diagnostic assay.

In a further embodiment the invention provides a method for detecting a virus said method comprising:
  providing a single flat based well in accordance with the invention as described herein seeded with a cell line suitable for virus inoculation;
  specific pre-treatment of a specimen to obtain a sample that potentially contains a virus to be detected;
  inoculating the cell line with the sample;
  incubating the inoculated cell line;
  replacing sample media of the inoculated cell line with a virus recovery media comprising a cell culture medium supplemented with at least one hormone and at least one enzyme;
  incubating the inoculated cell line; and
  analyzing the incubated cell line for the presence of a virus.

It will be appreciated that in this method the sample media will typically be maintenance media which has been inoculated with the sample.

As used herein, the term "single flat-based well" includes within its scope a single well having any cross-sectional shape, provided that the base of the well that receives the specimen is flat.

In the context of the viral diagnostic aspects of the present invention the use of a single flat-based well ensures that the examination for viruses, using standard techniques such as inverted fluorescence or optical microscopy, provides more accurate results, as compared with for example examination of a sample located in the base of a well having a round or slightly curved base.

The single flat-based wells may be provided already seeded with a preselected cell line that will be determined, depending on its suitability for the growth and isolation of the particular virus or viruses to be analyzed for. For example, the cell line LLC-MK2 is suitable for detection of parainfluenza viruses, MDCK for influenza viruses; HEP-2 for Respiratory syncitial virus (RSV) and MRC-5 for cytomegalovirus (CMV), herpes simplex virus (HSV), Enteroviruses and Rhinoviruses. A skilled artisan could select the appropriate cell line for the growth and isolation of a given virus.

It will be recognized that the seeded single flat-based wells described herein may be provided in a form suitable for immediate use (i.e. a ready to use format), in the assay method of choice. One skilled in the art will appreciate that in a ready to use format the preselected cell line will usually be provided approximately 80-90% confluent. It will also be appreciated that the storage stability of such a preselected cell line will depend on the particular cell line provided.

Alternatively, the seeded single flat-based wells may be provided in a form suitable, for long-term storage. For example, the seeded flat-based wells may be provided frozen using standard techniques for the long-term preservation of cells. For example, but not limiting the cell freezing process in any way, the cells could be grown to a suitable confluency in the single flat-based wells and the growth medium replaced with a suitable storage medium. Following this step, the cells could be subjected to a cooling process and finally stored at −70-80 degrees Celsius. The storage medium may or may not contain a cryopreservative. The cryopreservative which may be added to the storage medium is not particularly limited but may include DMSO and/or serum. A person skilled in the art would be familiar with suitable cryopreservatives and their use. Not all cell lines can survive a freezing process and one skilled in the art will recognize which cell lines would be suitable and unsuitable in this regard.

It will be recognized that cell lines provided in a frozen format would then be subjected to an appropriate thawing process and the storage medium replaced with virus recovery medium. It will be appreciated by one skilled in the art that once thawed the cells would then usually be grown to 80-90% confluency before being used in the method of the invention as described herein.

Reference to the subject flat-based well being "seeded" with a cell line should be understood as reference to the well being pre-seeded with a preselected cell line prior to being provided for use in a viral diagnostic assay. Alternatively, the seeded wells may actually be seeded subsequent to being provided for use in a viral diagnostic assay. The step of seeding the wells may include sub-steps of depositing the preselected cell line diluted in growth medium in the wells, incubating the cells in a $CO_2$ incubator until the cells reach about 80-90% confluency and replacing the growth medium with maintenance medium.

It will be appreciated that, when multiple wells are to be compared directly for the growth and isolation of a particular virus, the volume of media in each well should be identical.

In certain embodiments, a plurality of wells are seeded with a preselected cell line to provide an array of wells, for example a conventional 12×8 array for a 96 well plate, or a 6×8 array for a 48 well plate. Alternatively, if desired a larger array, such as a 14×8 array may be provided. The number of wells provided is not particularly limited. It will be appreciated that if such arrays are provided, different cells will generally be seeded in different columns of the array, again depending on the viruses to be detected.

It will be appreciated that pre-seeded single flat-based wells of the invention may be provided suitably sealed to enable transportation and to prevent contamination and evaporation. For example, in the case of a plurality of wells the seal could take the form of a cover which fits over the full array of wells, such as a standard 48 or 96 well plate cover. Alternatively, in the case of a single flat-based well, the seal may take the form of a suitable cap which seals the individual well. In another alternative, the seal may be a suitable sealing membrane.

It will also be appreciated that the cover either for a plurality of wells or for a single flat-based well in accordance with the invention as described herein may contain markings to assist in use. For example, the cover may contain a symbol or letter representing the cell line contained within.

The step of inoculating the specimen to be analyzed in the one or more cells is conducted in accordance with known procedures. For example, this will generally involve removing an appropriate amount of maintenance medium from each well to be inoculated, and depositing an amount, generally about 200-300 μl, of specimen supernatant into each well. The wells may then be centrifuged/incubated, for example at 4000 rpm at 35° C. for about 50-60 minutes depending on the type of centrifuged used.

After being removed from the centrifuge, inoculum may be removed from the wells, for example by vacuum aspiration, and replaced with a suitable maintenance medium or virus recovery medium. This preferably includes cell culture media supplemented with a hormone and an enzyme.

As used herein, the term "a specimen to be analysed" includes sample specimens obtained from subject that may or may not be infected with a virus. Therefore the sample may contain a detectable virus or may be virus free. Suitable samples may be obtained from saliva, serum, urine, feces, cerebrospinal fluid (CSF), respiratory fluids such as bronchial alveolar lavages and nasopharyngeal aspirates, and swabs such as those from the mouth, nasal cavity, throat, skin and genitals. The sample specimen may be prepared for use by dilution with a suitable media that is compatible with the cell line and virus.

The subject may be any species of animal that may be infected with a virus. For example, the subject may be a bird, fish or mammal. In some embodiments, the subject is a mammal. Suitable mammals include farmed animals such as sheep, cattle, pigs, deer and the like, companion animals such as dogs, cats, rabbits, guinea pigs and the like, laboratory animals such as mice, rats, monkeys and the like, captive animals such as those kept in zoos and humans. Preferred mammals are humans. In other embodiments, the subject may be a bird, particularly farmed birds such as chickens and turkeys. Specific pre-treatment methods of specimens to obtain samples suitable for virus detection are well known by the skilled artisan but may include, without being limited to, sonication and centrifugation.

As used herein, the terms "virus recovery medium" or "virus recovery media" refers to a medium or media which is used for virus growth and isolation. For example, virus recovery medium includes maintenance medium. It has been found by the present inventor that a cell culture media which is dosed with both hormone and enzyme advantageously optimizes virus recovery by maintaining cell line sensitivity at its maximum as well as aiding in the attachment of viruses to the cell wall and in some cases reducing the time taken to obtain a result.

The enzyme added to the cell culture medium is not limited and a person skilled in the art could identify suitable enzymes. In some embodiments, the term "enzyme" refers to a proteolytic enzyme. In these embodiments, the enzyme is preferably a serine or aspartate protease. Exemplary enzymes include trypsin, chymotrypsin or pepsin. In preferred embodiments, the enzyme is trypsin.

The hormone added to the cell culture medium is not limited and a person skilled in the art could identify suitable hormones. In some embodiments, the term "hormone" refers to corticosteroids, preferably, a glucocorticoid. More preferably, the hormone is selected from dexamethasone, hydrocortisone, cortisone acetate, prednisone, prednisolone, methylprednisolone, betamethasone, triamcinolone, beclomethasone, fludrocortisone acetate, deoxycorticosterone acetate (DOCA), and aldosterone. In a preferred embodiment, the hormone is dexamethasone. The hormone may be either synthetic or naturally occurring.

While the combination of hormone and enzyme is the most preferred embodiment, alternatively it has been found that DMSO (dimethylsulfoxide) and DEAE (dextran) may also be useful.

The amount of the enzyme added to the culture medium is preferably within the range 1-5 μg/ml, and preferably about 2.5 μg/ml. The concentration of hormone in the culture medium is preferably within the range $10^{-4}M$-$10^{-6}M$ and preferably about $10^{-5}M$. However, in the case of dexamethasone and trypsin, which are preferred, it has been found that a cell culture media supplemented with about 2.5 μg/ml trypsin and dexamethasone at a concentration of about $10^{-5}M$ gives the optimum result.

Accordingly, a specific embodiment of the method of the invention employs a virus recovery medium that includes a cell culture media supplemented with 2.51 μg/ml trypsin and dexamethasone at a concentration of $10^{-5}M$.

The cell culture media which may be used in accordance with the invention is not particularly limited. For example, these may include medium-199, DMEM, RPMI-1640 or MEM-EAGLE. As will be readily recognized, however there is a wide variety of different media which can support the growth of cells and which are readily available to the skilled artisan. However, according to a preferred embodiment the cell culture media is MEM-EAGLE.

The cell culture media may be supplemented with additives that support cell and virus growth and such additives are known to those skilled in the art. It is known that particular cell lines and/or viruses may require specific additives for optimal growth and viability. Exemplary additives include L-glutamine, amino acids, antibiotics, serum, Hanks balanced salts, sugars such as D-glucose, inorganic salts, vitamins, phenyl red, buffers such as HEPES and surfactants such as Tween 80.

The Virus recovery medium described above may be used in conventional diagnostic procedures for identifying viruses such as the conventional tube method and the shell vial method. Alternatively, the virus recovery medium may be used in the method of the invention as described herein.

The virus recovery medium used in the method of the invention may be used for the recovery of a number of different viruses which are suitable for cell culture. The skilled artisan will recognize that such viruses include, but are not limited to, the respiratory viruses, Parainfluenza 1,2,3,4 (PI 1,2,3,4), Influenza A,B (Inf A,B), Respiratory syncitial virus (RSV), Adenovirus (AD), Rhinovirus (RH), Cytomegalovirus (CMV), and viruses from the Enterovirus group (ENT) consisting of Echovirus, Coxakievirus, Enterovirus and Poliovirus, and also non-respiratory viruses such as, but not limited to, Herpes simplex virus (HSV) 1,2, Varicella zoster virus (VZV), Rubella, mumps, measles, rotavirus and polyomavirus.

In the method of the invention the inoculated cells may be incubated with the specimen to be analyzed using known conditions. For example, the inoculated cells may be incubated at 37° C. for a period that results in the infection of the cells with the virus, such as 45 to 90 minutes, especially 60 minutes. Incubation may be performed in an incubator or may be performed with centrifugation.

The virus may be detected using common detection methods known in the art such as immunodetection techniques such as immunofluorescence, staining, visualization of CPE, commonly used molecular techniques such as polymerase chain reaction (PCR), reverse transcriptase PCR (RT-PCR) and nucleic acid sequence based amplification (NASBA).

In order to prepare the wells for examination, a number of washing steps are generally employed in accordance with conventional methodology. For example, maintenance medium is generally removed and the cells are air dried in the wells. The wells may then be filled with, for example a cold methanol-acetone mixture (1:2 ratio) and fixed for 15 minutes at −25° C. After the mixture is removed, the wells may again be air dried. Specific monoclonal antibodies may then be added to each of the wells, depending on the virus to be detected, and the wells incubated as needed. The monoclonal antibodies may then be discarded and the wells again washed. This process may be repeated with secondary antibodies.

After a final air drying, 1-2 drops of fluorescent mounting medium may be added to the well and the contents examined for immunofluorescence.

Reference will now be made to the accompanying drawings which illustrate embodiments of the present invention.

Figure 1:
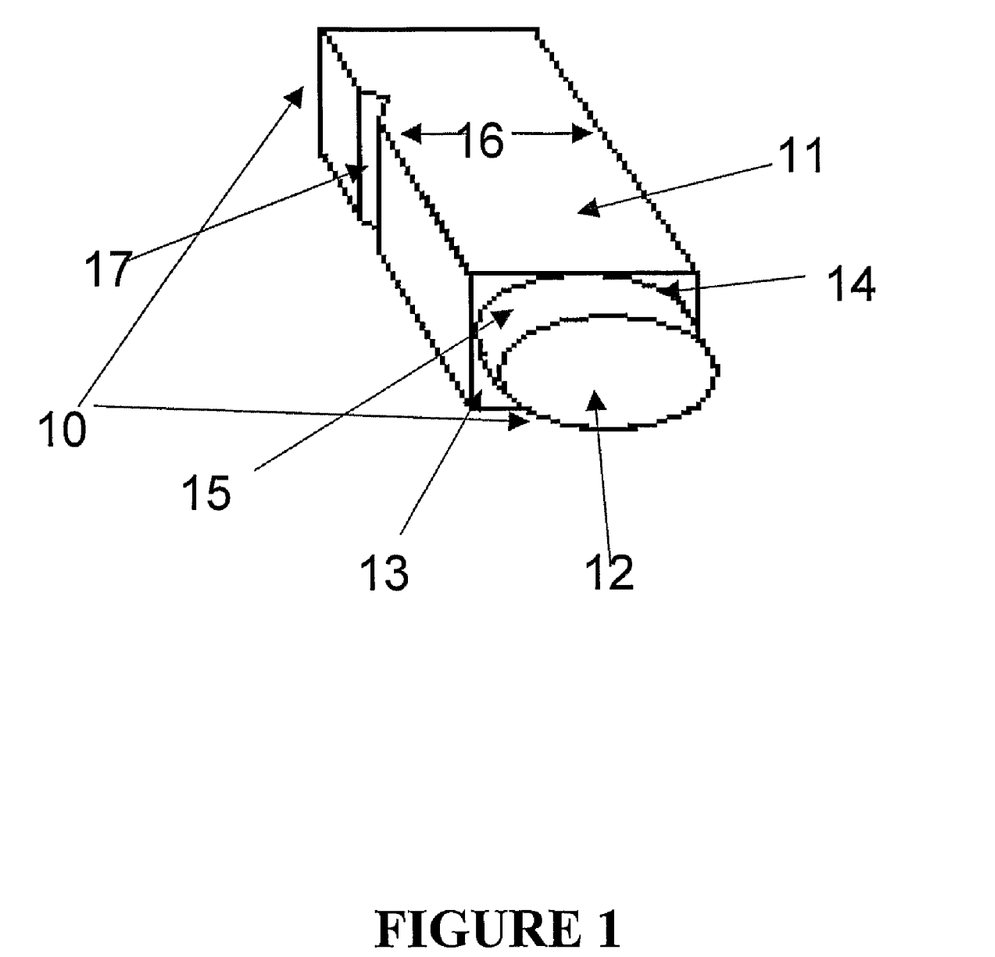
FIG. 1 is a schematic representation which illustrates a perspective view of the well.
Figure 3:
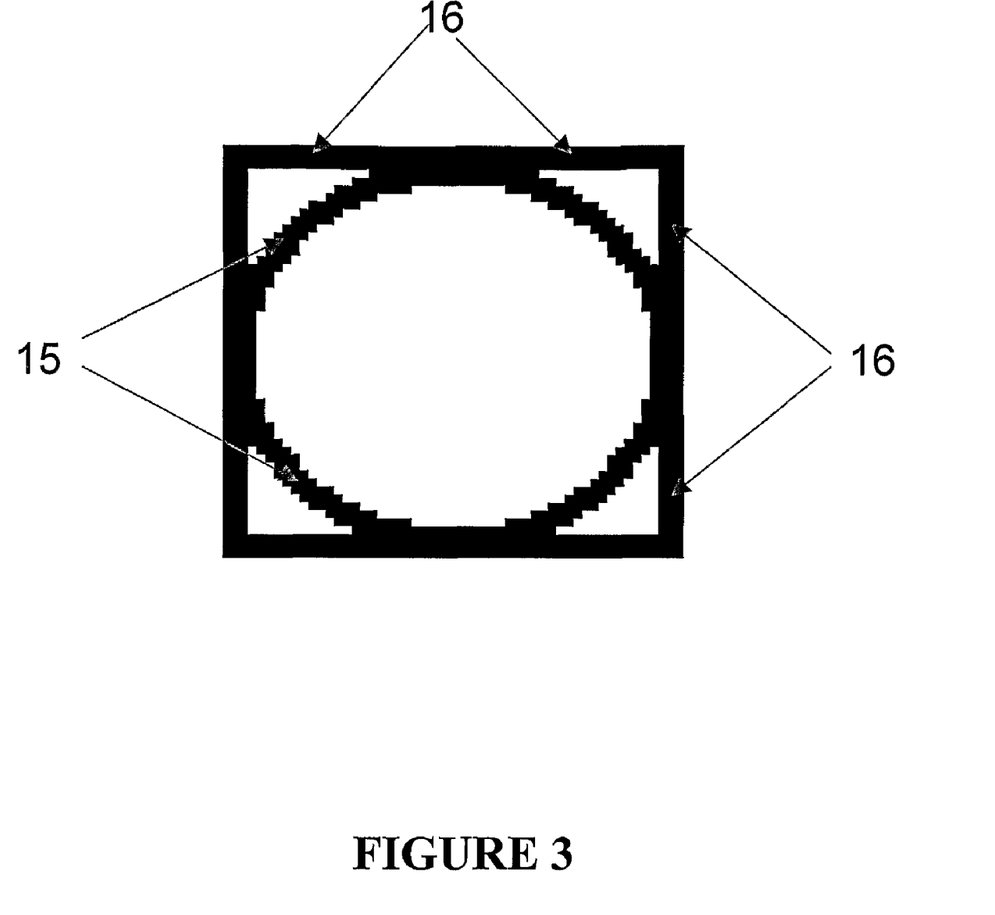
FIG. 3 is a schematic representation which illustrates a bottom view of the well.

Referring to FIG. 1, a particularly preferred embodiment of the flat-based well 10 to be used in accordance with the invention includes a main chamber 11 that is square in cross section, and a sub-chamber 12 that is circular in cross section. The sub-chamber 12 extends from a chamber base 13 of the main chamber 11. As such the opening 14 of the sub-chamber is defined by the chamber base 13 of the main chamber. The arc of the outer wall 15 of the sub-chamber 12 extends to the outer sides of each wall 16 of the main chamber 11 (best illustrated in FIG. 3).

One wall 16 of the main chamber 11 includes a groove 17 for receiving a cooperating portion of a well plate (not shown) into which the well 10 is to be placed. This facilitates secure locking of the well 10 in the plate and alleviates problems associated with wells 10 being dislodged from the plate.

The sub-chamber 12 has a predetermined volume so that it receives a liquid sample and forms the liquid sample into a droplet advantageously having a convex surface extending from the sub-chamber opening 14. This ensures that the depth of the liquid is substantially constant through the sub-chamber, as compared with a liquid sample that is placed in a well and forms a meniscus up the side walls of the well. In that case, the depth of liquid on the sides of the well where the meniscus forms will be substantially greater than that in the middle of the well where the meniscus is at its lowest point.

Figure 2:
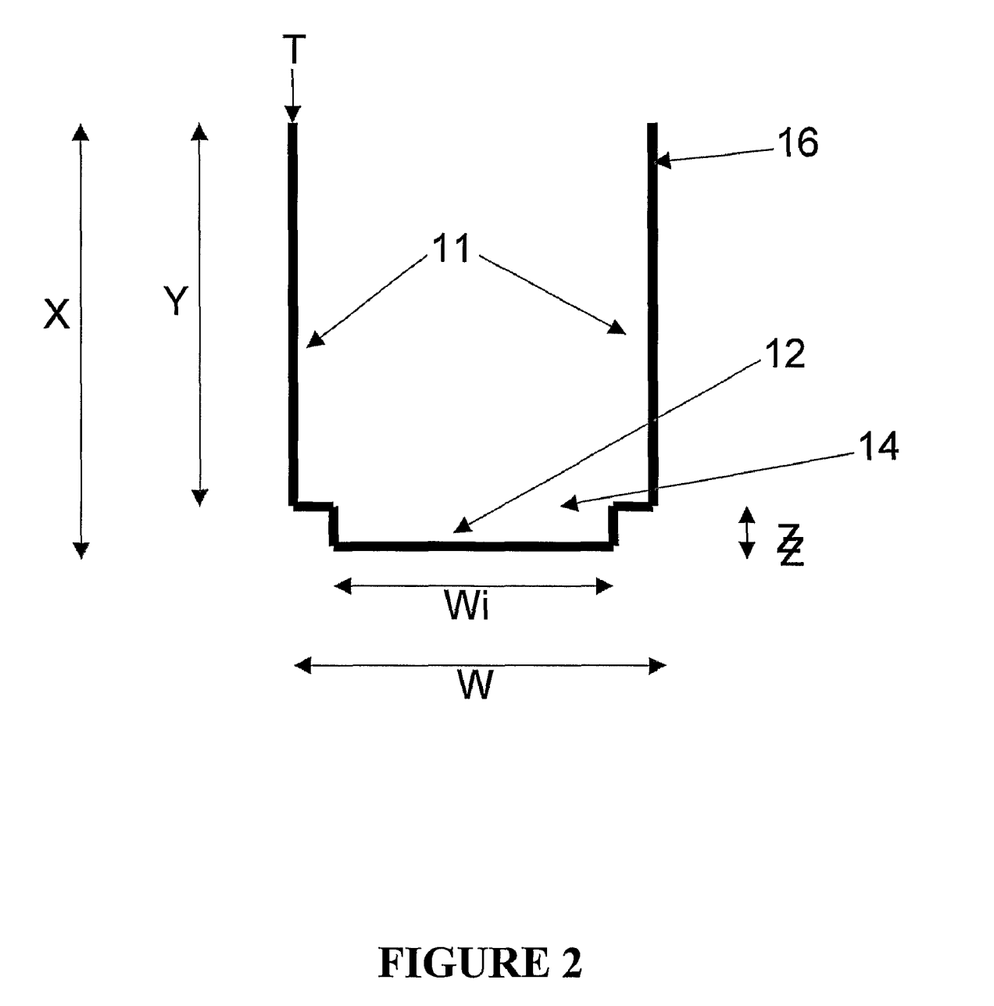
FIG. 2 is a schematic representation which illustrates a sectional side view of the well.

Preferably, the height X of the well is 11 mm, including a 10 mm height Y for the main chamber and a 1 mm depth Z for the sub-chamber. The well is generally 8 mm across its width W, and has a wall thickness T of about 1 mm. Thus, the internal width Wi is about 6 mm. The main chamber typically defines a volume of about 360 µl and the sub-chamber a volume of about 28.3 µl.

Figure 4:
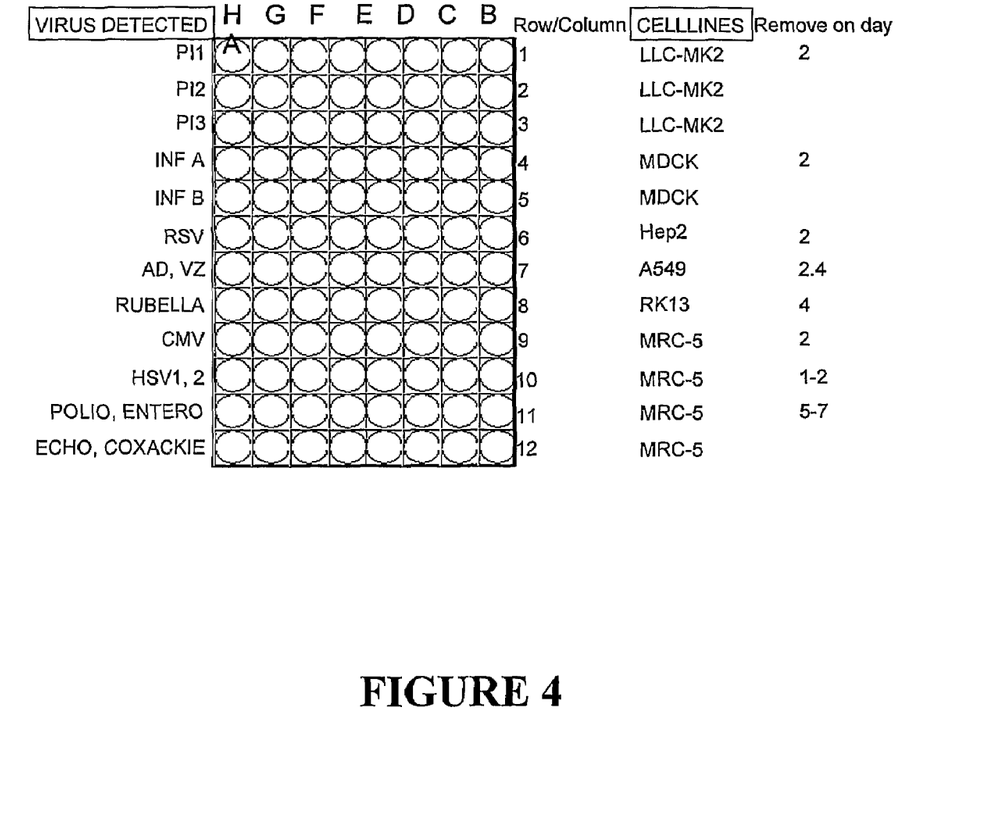
FIG. 4 is a schematic representation which illustrates a typical well configuration for a 12×8 array.

FIG. 4 exemplifies one example of a typical 12×8 well plate configuration (i.e. 2×6×8) including a listing of viruses to be detected, relevant cell lines and removal days for each line. The plate is made up of 96 individual flat-based wells in accordance with the present invention.

As will be seen from FIG. 4, the plate can be seeded with different cell lines in the following order:

| | |
|---|---|
| Columns 1-3 | LLC-MK2 |
| Columns 4,5 | MDCK |
| Column 6 | Hep2 |
| Column 7 | A549 |
| Column 8 | RK13 |
| Columns 9-12 | MRC-5 |

A plate set up in this fashion would allow for example the selection of, without being limited to, the respiratory viruses Parainfluenza 1,2,3,4 (PI 1,2,3,4), Influenza A,B (Inf A,B) RSV, Adenovirus (AD), Rhinovirus (RH), Cytomegalovirus (CMV), and viruses from the Enterovirus group (ENT) consisting of Echovirus (Eco), Coxsackievirus (cox), Enterovirus (Ent) and Poliovirus (Polio), as well as, but not limited to, the non-respiratory viruses Herpes simplex virus (HSV) 1,2, and Varicella zoster virus (VZV).

In a further example, configuration of a 6×8 well plate may consist of cell lines seeded in the following order:

| | |
|---|---|
| Columns 1-3 | A 549 |
| Columns 4-6 | MRC-5 |

This would allow for example the detection of viruses such as CMV, HSV 1,2, VZV, AD, and those from the Enterovirus group.

Finally a configuration of 14×8 wells would ultimately allow for the detection of pathogens like PI 1,2,3,4; Inf A,B; RSV; AD; RH; ENT (Echo, cox, Ent, Polio); HSV 1,2; VZV; Rubella; Mumps; Measles; Rotavirus; Polyomavirus and also other pathogens-viruses using appropriate cell lines.

The removal of the cell lines, due to the individual nature of the wells, can be selective depending on the time schedule which is appropriate for the specific viral detection in question. In particular, if the detection of PI 1-4 is desired, taking row A for example, wells A 1 to A 3 are removed on day two. Similarly, if the detection of Inf A, B is desired, wells A 4 and A 5 are removed on day two. However, if the detection of Entero is required, then well A 11 is removed on the appropriate day (1-3). The specific nature of the individual wells facilitates this selective removal and viral detection.

Reference will now be made to a particular procedure which may be followed using the kit of one aspect of the invention, many steps of which may be optional and should not be considered to be limiting on the invention in any way.

Using vacuum and sterile glass pasteur pipettes, medium is aspirated from all wells to be inoculated. Disposal of pasteur pipettes in a large sharps container is advantageously facilitated.

Using a disposable pipette, an appropriate number of wells of the well plate are inoculated with approximately 150-200 µl specimen per well. The remaining specimen is stored at −70° C. The lid is then replaced on the plate and the date written over the wells inoculated in the plate.

The plate is then weighed on a digital balance and balanced with balance plates and cards until all plates are equivalent weights (+/−0.5 g) and can be balanced in a centrifuge. The centrifuge is run at about 37° C. and 3500 rpm for a period of 60 min. Using vacuum and sterile pasteur pipettes each specimen is then aspirated from each well, and using a fresh disposable pipette for each specimen, each well is filled with the virus recovery medium BAC.

The specimens are then incubated in a humidified environment at 37° C. in a $CO_2$ incubator (5%) by carefully placing the plates in the $CO_2$ incubator and incubating at 37° C. for up to seven days after inoculation of the last specimen.

Immunofluorescent staining is advantageously used for detection of specific viruses in single wells, using specific monoclonal antibodies. Generally, the following procedure is followed:

Using vacuum suction, the medium is removed from the appropriate well(s) and the wells removed from the plate using special forceps and transferred into a different holder. These are then air dried for 3 minutes. 300 µl of a mixture of cold acetone and methanol (2:1) is then added to each well and allowed to fix for 15 minutes at −20° C. The fixative is then discarded and the sample again air dried for 2-3 minutes. A specific monoclonal antibody (primary) is then added to each well and the cover plate put in place and the samples incubated for 30 minutes at 37° C. The samples are then removed from the incubator and each well filled with Phosphate Buffered Saline (PBS). The PBS is then discarded. This process is repeated four more times. Again, the sample is air dried for 3 minutes, after which a secondary antibody specific for the primary antibody is added to each well. Following this, incubation of the sample again takes place followed by repeated treatments with PBS as mentioned above and a final wash with double distilled water. A small amount (1 drop) of a specially prepared mounting medium is then added and the results observed under fluorescent microscope. One step immunofluorescent staining may also be employed.

Throughout this specification and the claims which follow, unless the context requires otherwise, the word "comprise", and variations such as "comprises" and "comprising", will be understood to imply the inclusion of a stated integer or group of integers or steps but not the exclusion of any other integer or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A single flat-based well suitable for use in viral detection assays, the well comprising:
   (i) a main chamber having an opening to receive a liquid sample; side walls which extend from the opening and a chamber base; and
   (ii) a sub-chamber extending from below the chamber base of the main chamber, the sub-chamber is seeded with a frozen or ready to use preselected cell line in a virus recovery medium and is adapted to receive a predetermined amount of the liquid sample and having a flat base;
   wherein the sub-chamber has a circular cross-section and the main chamber has a square cross-section.

2. A single flat-based well according to claim 1, wherein the well is provided with an engagement means for facilitating engagement with a well plate into which the well is to be inserted.

3. A single flat-based well of claim 2, wherein the well is tapered to provide a friction fit in a receptacle of a well plate.

4. A single flat-based well of claim 2, wherein the well is provided with a rib or an indentation or groove that cooperates with a receptacle of the well plate.

5. A single flat-based well according to claim 1, wherein the well includes a form of identification.

6. A single flat-based well according to claim 5, wherein the flat-base is provided with marked divisions adapted to assist analysis.

7. A single flat based well according to claim 1, wherein an arc of a circular side of the sub-chamber extends to an edge of each side of the main chamber.

8. A single flat-based well according to claim 1, wherein a ratio of a height of the main chamber compared to a height of the sub-chamber is 10:1 and a ratio of a width of the main chamber compared to a width of the sub-chamber is between 2:1 and 1:1.

9. A single flat-based well according to claim 1, wherein a height of the well is 11 mm, including a 10 mm height for the main chamber and a 1 mm depth for the sub-chamber.

10. A single flat-based well according to claim 1, wherein a width of the well is 8 mm, the well having a wall thickness of about 1 mm and an internal width of the sub-chamber is about 6 mm.

11. A single flat-based well according to claim 1, wherein the sub chamber receives a pre-determined amount of the liquid sample to a maximum volume of 30 µl.

12. A single flat-based well according to claim 1, wherein a ratio of volume between the main chamber and the sub-chamber is 12:1.

13. A single flat-based well according to claim 1, wherein the liquid sample in the sub-chamber forms a convex surface droplet extending from a sub-chamber opening, the liquid sample having a depth that is substantially constant through the sub-chamber.

14. A single flat-based well according to claim 1, further comprising a cap suitable to seal the well and provide a surface for additional markings.

15. A single flat-based well according to claim 6, wherein the marked divisions divide the flat-base into four quarters to assist analysis.

16. A single flat-based well accordingly to claim 1, wherein the chamber base is substantially flat and the sub-chamber extends substantially perpendicular to the chamber base.

* * * * *